United States Patent
Matsumoto et al.

(10) Patent No.: US 9,867,711 B2
(45) Date of Patent: Jan. 16, 2018

(54) VERTEBRAL BODY SPACER

(75) Inventors: Toshio Matsumoto, Tokyo (JP); Yuzo Daigo, Saitama (JP); Shinichi Ohmori, Saitama (JP); Komei Kato, Saitama (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 20 days.

(21) Appl. No.: 13/884,424

(22) PCT Filed: Nov. 9, 2011

(86) PCT No.: PCT/JP2011/075832
§ 371 (c)(1),
(2), (4) Date: Jul. 2, 2013

(87) PCT Pub. No.: WO2012/063863
PCT Pub. Date: May 18, 2012

(65) Prior Publication Data
US 2013/0274885 A1    Oct. 17, 2013

(30) Foreign Application Priority Data
Nov. 10, 2010 (JP) .................................. 2010-252228

(51) Int. Cl.
*A61F 2/44* (2006.01)
*A61F 2/28* (2006.01)
*A61F 2/30* (2006.01)

(52) U.S. Cl.
CPC .............. *A61F 2/442* (2013.01); *A61F 2/447* (2013.01); *A61F 2/4465* (2013.01);
(Continued)

(58) Field of Classification Search
None
See application file for complete search history.

(56) References Cited

U.S. PATENT DOCUMENTS

| 5,458,643 A | 10/1995 | Oka et al. |
| 6,379,385 B1 | 4/2002 | Kalas et al. |

(Continued)

FOREIGN PATENT DOCUMENTS

| EP | 1477190 A1 | 11/2004 |
| EP | 2453937 A2 | 5/2012 |

(Continued)

OTHER PUBLICATIONS

International Search Report dated Feb. 14, 2012, issued for PCT/JP2011/075832.

*Primary Examiner* — David Isabella
*Assistant Examiner* — Christine Nelson
(74) *Attorney, Agent, or Firm* — Locke Lord LLP

(57) ABSTRACT

A vertebral body spacer of the present invention is used by being inserted between a vertebral body and a vertebral body (intervertebral space). The vertebral body spacer has a block body constituted of titanium or a titanium alloy as a main component thereof, and provided with a pair of contact surfaces to be made contact with the vertebral body and the vertebral body. The block body includes a frame-shaped dense part and a porous part provided inside the dense part, and a porosity of at least a surface of the porous part is larger than a porosity of the dense part. According to the present invention, it is possible to maintain an appropriate size between the vertebral bodies (intervertebral space).

8 Claims, 8 Drawing Sheets

(52) U.S. Cl.
CPC ............ *A61F 2002/2817* (2013.01); *A61F 2002/2835* (2013.01); *A61F 2002/30011* (2013.01); *A61F 2002/30013* (2013.01); *A61F 2002/3092* (2013.01); *A61F 2002/30471* (2013.01); *A61F 2002/30472* (2013.01); *A61F 2002/30616* (2013.01); *A61F 2002/30629* (2013.01); *A61F 2002/30784* (2013.01); *A61F 2002/30841* (2013.01); *A61F 2002/30971* (2013.01); *A61F 2002/448* (2013.01); *A61F 2002/4475* (2013.01); *A61F 2310/00023* (2013.01); *A61F 2310/00029* (2013.01); *A61F 2310/00089* (2013.01); *A61F 2310/00095* (2013.01); *A61F 2310/00131* (2013.01)

(56) References Cited

U.S. PATENT DOCUMENTS

| | | | |
|---|---|---|---|
| 6,423,095 | B1 * | 7/2002 | Van Hoeck ............ A61F 2/442 606/247 |
| 8,119,152 | B2 | 2/2012 | Shikinami |
| 8,361,150 | B2 | 1/2013 | Zhang et al. |
| 2001/0001129 | A1 * | 5/2001 | McKay et al. ............ 623/17.16 |
| 2001/0010021 | A1 | 7/2001 | Boyd et al. |
| 2002/0169066 | A1 | 11/2002 | Cassidy et al. |
| 2004/0010312 | A1 | 1/2004 | Enayati |
| 2004/0258732 | A1 | 12/2004 | Shikinami |
| 2005/0038513 | A1 | 2/2005 | Michelson |
| 2005/0065604 | A1 | 3/2005 | Stoll |
| 2005/0159815 | A1 | 7/2005 | Kamimura et al. |
| 2006/0173542 | A1 | 8/2006 | Shikinami |
| 2009/0162235 | A1 | 6/2009 | Kita et al. |
| 2009/0204214 | A1 | 8/2009 | Fuji et al. |
| 2009/0317278 | A1 | 12/2009 | Kokubo |
| 2011/0054616 | A1 | 3/2011 | Kamran et al. |
| 2011/0190888 | A1 | 8/2011 | Bertele et al. |

FOREIGN PATENT DOCUMENTS

| | | |
|---|---|---|
| JP | 04-303444 A | 10/1992 |
| JP | 10-033656 A | 2/1998 |
| JP | 2001-046489 A | 2/2001 |
| JP | 2002-095685 A | 4/2002 |
| JP | 2003-230583 A | 8/2003 |
| JP | 2007-151805 A | 6/2007 |
| JP | 2007-236803 A | 9/2007 |
| WO | WO-2008/026316 A1 | 3/2008 |
| WO | WO-2010/019799 A1 | 2/2010 |
| WO | WO-2010/021612 A1 | 2/2010 |
| WO | WO-2011/008733 A2 | 1/2011 |

* cited by examiner

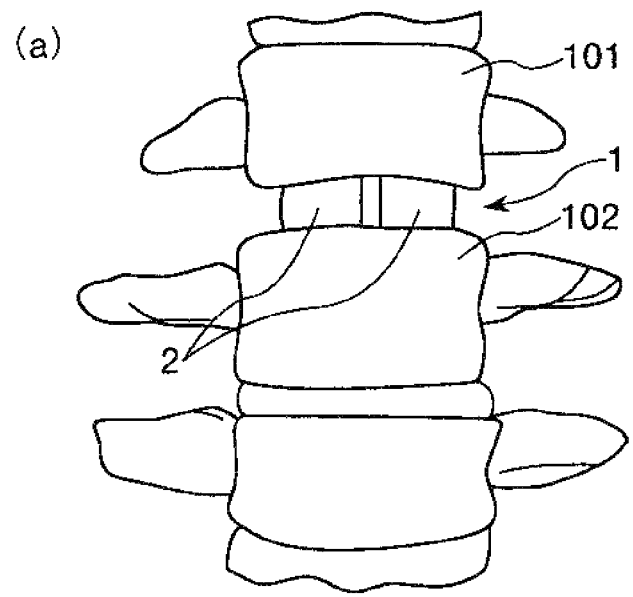
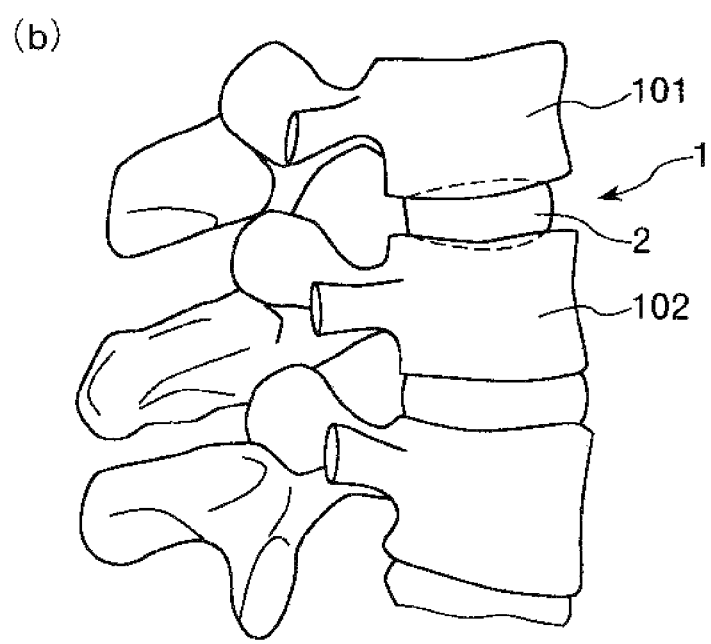
FIG.2

VERTEBRAL BODY SPACER

CROSS REFERENCE TO RELATED APPLICATIONS

This application is related to co-pending application, entitled, "VERTEBRAL BODY SPACER" filed concurrently herewith in the names of Toshio Matsumoto, Yuzo Daigo, Shinichi Ohmori and Komei Kato as a national stage application of International Application Nos. PCT/JP2011/075841 and PCT/JP2011/075836 filed Nov. 9, 2011, which application is assigned to the assignee of the instant application and which co-pending application is also incorporated by reference herein.

TECHNICAL FIELD

The present invention relates to a vertebral body spacer.

RELATED ART

Spinal canal stenosis is caused by degeneration of an intervertebral disk interposed between adjacent vertebral bodies (intervertebral space), degenerative facet joint disease, secondary deformation of a vertebral body, spinal deformation, or the like, and results in cauda equina/nerve root disorders.

One approach for treating such spinal canal stenosis includes interbody fusion in which a degenerated intervertebral disk is removed from between the adjacent vertebral bodies, and then used is an vertebral body fusion surgery of fusing the vertebral bodies by implanting an autologous bone into an intervertebral space in which the intervertebral disk has been removed.

However, in a case where only bone grafting into the intervertebral space is carried out, there is a possibility that unstable fusing between the vertebral bodies is caused by resorption of a grafted bone until bone fusion is achieved. Further, an amount capable of harvesting an autologous bone is limited, so that there is a possibility that a bone to be grafted is not acquired in a sufficient amount.

Therefore, used is a method of fusing the vertebral bodies stably by inserting a vertebral body spacer by itself as a substitute material of an autologous bone or the vertebral body spacer together with the autologous bone into the intervertebral space.

In this case, it is required that this vertebral body spacer supports vertebral bodies stably and fuses with the vertebral bodies easily. From a point of such a view, a constituent material and a shape of the vertebral body spacer have been studied, so that various kinds of vertebral body spacers have been developed (for example, Patent Document 1).

Such a vertebral body spacer, generally, is constituted from a block body having a uniform porosity. Such a porosity is set to fall within the range of about 30 to 60% for a purpose of achieving bone fusion between the vertebral body spacer and vertebral bodies making contact with the vertebral body spacer promptly.

However, it is impossible for the vertebral body spacer having the porosity falling within such a range to withstand stress on the vertebral body spacer depending on a body type of a patient to which the spacer is to be applied and a position of an intervertebral space such as lumbar vertebra and cervical vertebra. As a result, there is a fear that the vertebral body spacer is broken by the stress.

Patent Document: JP 2002-95685 A

SUMMARY OF THE INVENTION

It is an object of the present invention to provide a vertebral body spacer that is capable of maintaining an appropriate size between vertebral bodies (intervertebral space) and reliably preventing the vertebral body spacer from being broken irrespective of cases and a position of the intervertebral space, and thereby capable of achieving bone fusion between the vertebral body spacer and vertebral bodies promptly.

The object is achieved by the present inventions (1) to (8) described below.

(1) A vertebral body spacer to be used by being inserted between vertebral bodies, comprising;
at least one block body constituted of titanium or a titanium alloy as a main component thereof, and the block body having a pair of contact surfaces to be made contact with the vertebral bodies, and
wherein the block body includes a frame-shaped dense part and a porous part provided inside the dense part, and a porosity of at least a surface of the porous part is larger than a porosity of the dense part.

This makes it possible to maintain a suitable size between the vertebral bodies (intervertebral space). Further, it is possible to reliably prevent the block body from being broken irrespective of cases (patients) and a position of the intervertebral space, and thereby capable of achieving bone fusion between the block body and the vertebral bodies promptly.

(2) In the vertebral body spacer in above-mentioned item (1), the dense part and the porous part are integrally formed.

According to the vertebral body spacer mentioned above, in a state of inserting the block body into the intervertebral space, it is possible to reliably prevent stress from being applied to the dense part or the porous part unevenly when the stress is applied to the block body.

(3) In the vertebral body spacer in above-mentioned item (1), the porous part has a plurality of corner portions, and the dense part is provided along the plurality of corner portions of the porous part.

According to the vertebral body spacer mentioned above, the dense part is formed so as to define the whole shape of the block body.

(4) In the vertebral body spacer in above-mentioned item (1), the block body is constituted from a polyhedral body defined by a plurality of surfaces including the pair of contact surfaces, and each of the plurality of surfaces constitutes a flat surface.

This makes it possible to reliably make the porous part contact with the vertebral bodies. Therefore, it is possible to achieve the bone fusion between the porous part and the vertebral bodies promptly.

(5) In the vertebral body spacer in above-mentioned item (1), at least one block body is constituted from a pair of block bodies.

This makes it possible to change a position of the pair of block bodies, namely to position the pair of block bodies in a state of spacing front ends and back ends of the pair of block bodies from each other and/or approaching them to each other. Therefore, it is possible to provide an appropriate cure depending on cases by using such a vertebral body spacer.

(6) In the vertebral body spacer in above-mentioned item (1), a whole of the porous part is constituted from a porous body.

This makes it possible to achieve the bone fusion between the porous part and the vertebral bodies promptly. Therefore, it is possible to reliably fuse the block body in the intervertebral space.

(7) In the vertebral body spacer in above-mentioned item (1), an osteoinductive factor is carried on the porous part.

This makes it possible to achieve the bone fusion between the porous part and the vertebral bodies promptly.

(8) In the vertebral body spacer in above-mentioned item (1), the dense part includes a first frame portion to be made contact with one of the vertebral bodies, a second frame portion to be made contact with the other of the vertebral bodies and at least one connecting portion connecting the first frame portion and the second frame portion to each other, and wherein the connecting portion serves as a supporting post.

This makes it possible to improve strength of the dens part. Therefore, in a state of inserting the block body into the intervertebral space, it is possible to reliably suppress or prevent the dense part from being broken when the stress is applied to the block body.

According to the vertebral body spacer of the present invention, it is capable of maintaining the appropriate size between the vertebral bodies (intervertebral space). Further, it is possible to reliably prevent the vertebral body spacer from being broken irrespective of the cases and the position of the intervertebral space, and thereby capable of achieving the bone fusion between the vertebral body spacer and the vertebral bodies promptly.

Further, by inserting the vertebral body spacer into the intervertebral space, it is ensured to obtain a space for filling a filler into the intervertebral space. Therefore, by filling, for example, a grafted bone into such a space, it is possible to achieve the bone fusion between the vertebral bodies through the vertebral body spacer and the grafted bone more reliably and promptly.

BRIEF DESCRIPTION OF THE DRAWINGS

FIG. 2 is a view showing a used state of the first embodiment of the vertebral body spacer of the present invention.

BEST MODE FOR CARRYING OUT THE INVENTION

Hereinbelow, description will be made on a vertebral body space according to the present invention in detail with reference to preferred embodiments shown accompanied drawings.

First Embodiment

First, description will be made on a first embodiment of the vertebral body space according to the present invention.

Figure 1:
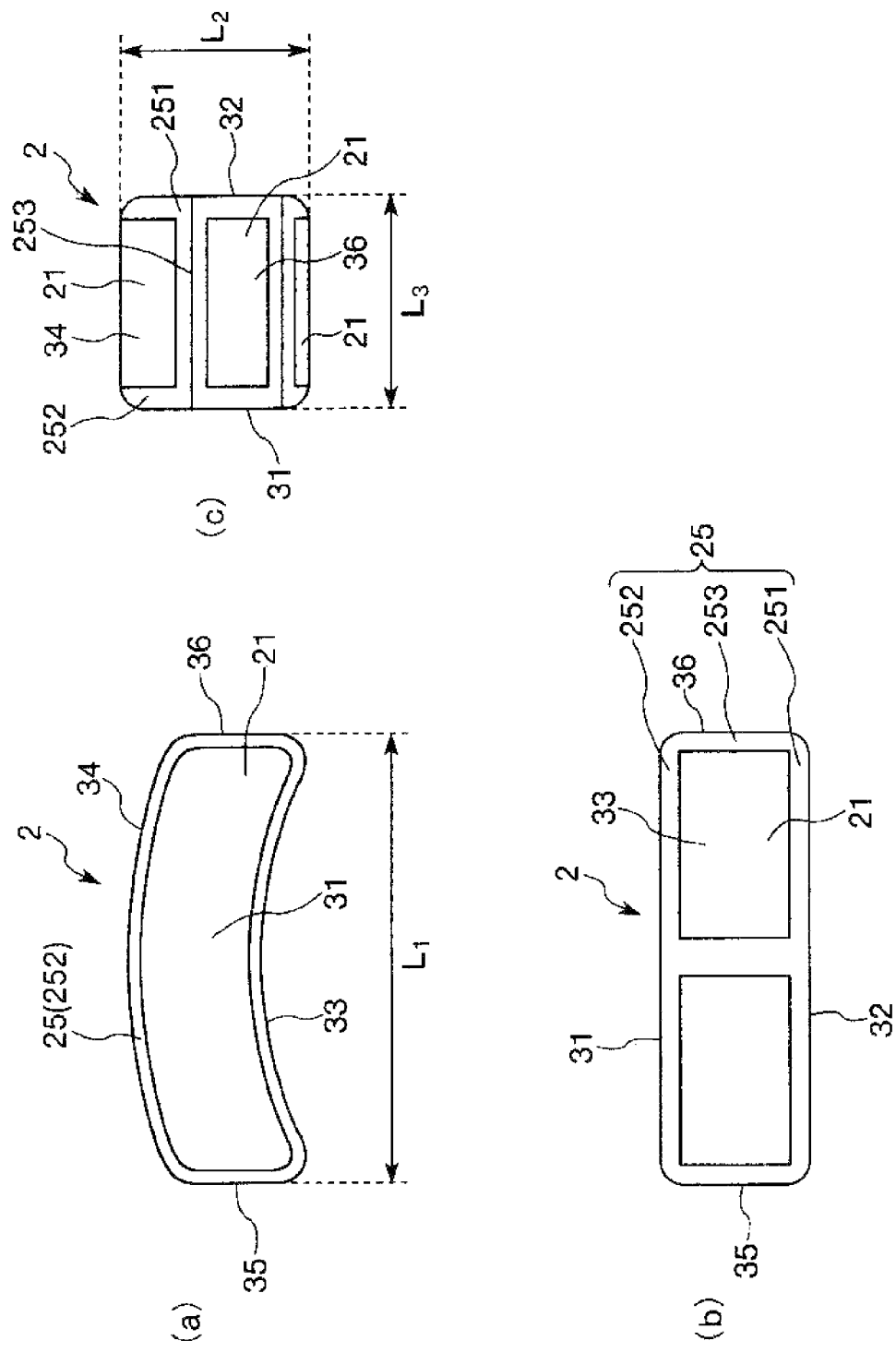
FIG. 1 is a plan view (a), a front view (b) and a side view (c) which show a first embodiment of a block body constituting a vertebral body spacer of the present invention.
Figure 3:
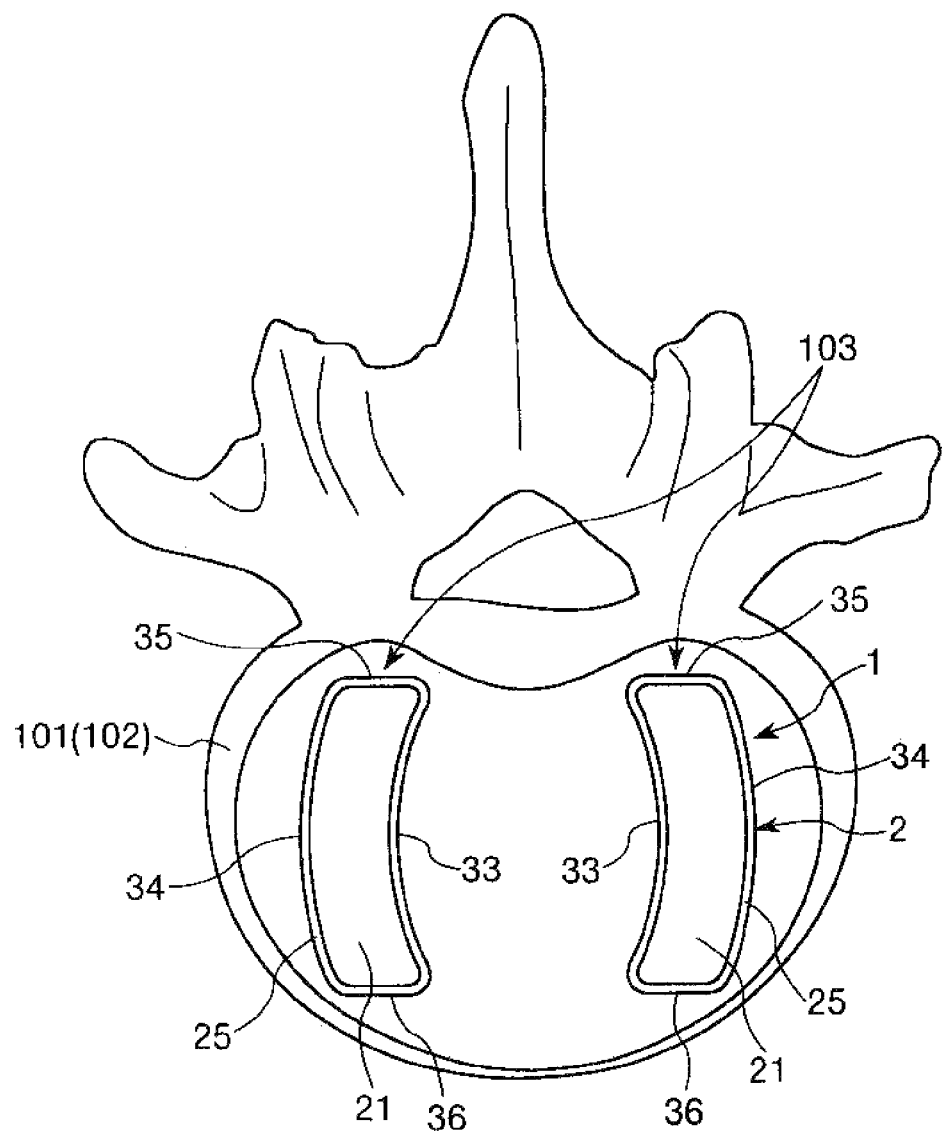
FIG. 3 is a view showing a used state of the first embodiment of the vertebral body spacer of the present invention.

FIG. 1 is a plan view (a), a front view (b) and a side view (c) which show the first embodiment of a block body constituting the vertebral body spacer of the present invention. FIG. 2 and FIG. 3 are a view showing a used state of the first embodiment of the vertebral body spacer of the present invention, respectively.

In the following description, it is to be noted that a state of inserting the vertebral body spacer between vertebral bodies of a case (patient) is defined as a basic state, thereby defining a position thereof, unless it is explicitly stated otherwise.

Specifically, a ventral side of the patient (namely, a right side in each of FIG. 1(a), FIG. 1(b) and FIG. 2(b), a near side in each sheet of FIG. 1(c) and FIG. 2(a), and a lower side in FIG. 3) will be referred to as "front", and a dorsal side of the patient (namely, a left side in each of FIG. 1(a), FIG. 1(b) and FIG. 2(b), a back side in each sheet of FIG. 1(c) and FIG. 2(a), and an upper side in FIG. 3) will be referred to as "back". Further, a head side of the patient (namely, an upper side in each of FIG. 1(b) and FIG. 2, a near side in each sheet of FIG. 1(a) and FIG. 3, and a left side in FIG. 1(c)) will be referred to as "upper", and a leg side of the patient (namely, a lower side in each of FIG. 1(b) and FIG. 2, a back side in each sheet of FIG. 1(a) and FIG. 3, and a right side in FIG. 1(c)) will be referred to as "lower". It is to be noted that a position of the vertebral body spacer in each of FIGS. 4 to 8 is also defined as the same as those in FIGS. 1 to 3.

As shown in FIG. 2, a vertebral body spacer 1 is inserted between a vertebral body 101 and a vertebral body 102 (hereinafter, referred to as "intervertebral space") at the time of fusing the upper vertebral body 101 and the lower vertebral body 102 after an intervertebral disk has been removed. It is ensured to maintain (hold) an appropriate space (distance) between the vertebral body 101 and the vertebral body 102 in a state of inserting the vertebral body spacer 1 into the intervertebral space (hereinafter, referred to as "inserted state").

In the present embodiment, as shown in FIG. 2(a) and FIG. 3, the vertebral body spacer 1 (hereinafter, simply referred to as "spacer 1") is constituted from a pair of elongated block bodies 2, 2. Each of the block bodies 2, 2 is substantially identical to each other in a shape (constitution).

As described above, each of the block bodies 2, 2 is substantially identical to each other in the shape. Therefore, hereinafter, the description will be made on one of the pair of elongated block bodies 2, 2 as a representative.

As shown in FIG. 1, the block body 2 is constituted from a polyhedral body which is formed from a plurality of surfaces having a first surface 31, a second surface 32, a third surface 33, a fourth surface 34, a fifth surface 35 and a sixth surface 36.

As shown in FIG. 3, the first surface 31 constitutes a contact surface to be made contact with the vertebral body 101 and the second surface 32 constitutes a contact surface making contact with the vertebral body 102 in a state of inserting the block body 2 into the intervertebral space (inserted state). Further, in the inserted state, the third surface 33 defines an inside space 103 in the intervertebral space and the fourth surface 34 defines an outside space 103 in the intervertebral space.

In the present embodiment, the third surface 33 constitutes a curved concave surface and the fourth surface constitutes a curved convex surface. This makes it possible to easily insert the block body 2 into the intervertebral space so as to correspond to shapes of the vertebral bodies (vertebral bone).

Further, the first surface 31, the second surface 32, the fifth surface 35 and the sixth surface 36 constitute substantially a plane surface (flat surface), respectively. Among of them, in particular, the plane surfaces (flat surfaces) of the first surface 31 and the second surface 32 make it possible to reliably be in the block body 2 contact with the vertebral bodies 101, 102.

Further, the first surface 31 and the second surface 32 have substantially an equal length. The third surface 33 and the fourth surface 34 also have substantially an equal length. The fifth surface 35 and the sixth surface 36 also have substantially an equal length.

In other words, the block body 2 is formed so that a cuboid is curved along a longitudinal direction thereof so as to concave the third surface 33 and convex the fourth surface 34.

In this regard, the vicinities of corner portions formed by making contact with each surface are chamfered, respectively. This makes it possible to prevent breakages such as a crack of the block body 2. In addition to that, it is possible to easily insert the block body 2 into the intervertebral space with making no contact with the vertebral bodies 101 and 102.

Dimension such as the length of such a block body 2 in a front-back direction ($L_1$ in FIG. 1), the length thereof in a horizontal direction ($L_2$ in FIG. 1) and the length thereof in an upper-lower direction ($L_3$ in FIG. 1) is arbitrarily dependent from a kind of vertebral body such as cervical vertebra and lumbar vertebra or cases. The dimension, however, is set to fall within ranges as follows.

The length of such a block body 2 in the front-back direction ($L_1$ in FIG. 1) is preferably set to the range of about 6 to 25 mm and more preferably the range of about 8 to 22 mm.

The length of the block body 2 in the horizontal direction ($L_2$ in FIG. 1) is preferably set to the range of about 4 to 25 mm, more preferably the range of about 10 to 25 mm and even more preferably the range of about 16 to 21 mm.

The length of the block body 2 in the upper-lower direction ($L_3$ in FIG. 1) is preferably set to the range of about 6 to 15 mm and more preferably the range of about 9 to 12 mm.

Meanwhile, the block body 2 of the present invention includes a frame-shaped dense part 25 and a porous part 21 provided inside the dense part 25. A porosity of at least a surface of the porous part 21 is larger than a porosity of the dense part 25. In other words, the block body 2 has the porous part 21 and the dense part 25 provided at an outer circumference side of the porous part 21. The configuration makes it possible to maintain a shape of the block body 2 due to the existence of the dense part 25 even if stress is applied to the block body 2 in the inserted state. Therefore, it is possible to reliably prevent or suppress the porous part 21 from being broken while maintaining an appropriate size of the intervertebral space. Further, it is ensured to achieve the bone fusion between the vertebral bodies 101, 102 and the porous part 21 promptly.

In the present embodiment, the dense part 25 has a lower frame portion (first frame portion) 251 and an upper frame portion (second frame portion) 252 which have a shape corresponding to the shape of the block body 2 in the plane view as shown in FIG. 1(a). The dense part 25 also has a plurality of connecting portions 253 which connect the lower frame portion 251 and the upper frame portion 252.

The configuration forms the dense part 25 defining the whole shape of the block body 2. In other words, the block part 2 has the porous part 21 having a plurality of corner portions and the dense part 25 formed along (so as to surround) the corner portions of the porous part 21. In the inserted state, the lower frame portion 251 is in contact with the vertebral body (one of the vertebral bodies) 102 and the upper frame portion 252 is in contact with the vertebral body (the other of the vertebral bodies) 101.

In the present embodiment, the plurality of connecting portions 253 includes four connecting portions provided at corner portions of each of the frame portion 251 and the frame portion 252, and two connecting portions provided at central portions of the frame portion 251 and the frame portion 252, respectively. Such connecting portions 253 have a function of supporting the lower frame portion 251 and the upper frame portion 252 as a supporting post. Therefore, in the inserted state, when stress is applied to the block body 2, it is possible to reliably prevent or suppress the lower frame portion 251 and the upper frame portion 252 from approaching to each other. In this regard, the porosity of the dense part 25 is not limited particularly, as long as the porosity is lower than that of the porous part 21. Specifically, the porosity of the dense part 25 is preferably in the range of about 3 to 50%, more preferably in the range of about 10 to 40% and even more preferably in the range of about 15 to 35%. It is noted that the porosity of the dense part 25 may be substantially 0%.

As described above, the connecting portions 253 exhibit the function as the supporting post and support the lower frame portion 251 and the upper frame portion 252. In this specification, such a structure is referred to as "supporting post structure".

The porous part 21 is configured to be filled into the frame-shaped dense part 25 and exposed to the surfaces 31 to 36 of the block body 2 from the inside of the dense part 25.

The porosity of at least the surface of the porous part 21 may be larger than the porosity of the dense part 25. Therefore, the porous part 21 may have a dense portion at the inside thereof. However, it is preferred the whole of the porous part 21 is constituted from a porous body. This constitution ensures to achieve the bone fusion between the vertebral bodies 101, 102 and the porous part 21 promptly. Therefore, the block body 2 is fused into the intervertebral space reliably.

The porosity of the porous part 21 is not limited particularly as long as the porosity of the porous part 21 is larger than the porosity of the dense part 25. Specifically, the porosity of the porous part 21 is in the range of about 20 to 95%, more preferably in the range of about 50 to 85% and even more preferably in the range of about 55 to 85%. This makes it possible to achieve the bone fusion between the vertebral bodies 101, 102 and the porous part 21 promptly. In the case where the porosity of the porous part 21 falls within such ranges, it is possible to reliably prevent or suppress the block body 2 from being broken when the stress is applied to the block body 2 in the inserted state. This is because the block body 2 has the dense part 25 in addition to the porous part 21. In this regard, it is to be noted that it becomes easy to form communicating holes, in which holes are connected with each other, in the porous part 21 if the porosity of the porous part 21 is equal to or larger than 55%.

Further, it is preferred that an osteoinductive factor is carried on inner surfaces of the communicating holes (holes) of the porous part 21. This makes it possible to achieve the bone fusion between the vertebral bodies 101, 102 and the porous part 21 promptly.

The osteoinductive factor is not limited particularly as long as it has an activity of promoting bone formation by deriving differentiated osteoblast from an undifferentiated mesenchymal cell. Specifically, bone morphogenic protein (BMP) is used preferably as the osteoinductive factor.

Examples of BMP include BMP-1, BMP-2, BMP-3, BMP-4, BMP-5, BMP-6, BMP-7, BMP-8, BMP-9, BMP-12 (these are a homodimer), a heterodimer of their BMPs or a modified body thereof, and the like.

In the present invention, the block body 2 can be produced by using a producing method as described later. According to such a producing method, it is possible to form the dense part 25 and the porous part 21 integrally. Such a block body 2 is capable of reliably preventing stress from unevenly being applied to the dense part 25 or the porous part 21 when the stress is applied in the inserted state. In this case, each of the surfaces 31, 32, 33, 34 constitutes the flat surface, namely a surface having no gap between the dense part 25 and the porous part 21. Therefore, it is possible to particularly make the porous part 21 contact with the vertebral bodies 101, 102 in the first surface 31 and the second surface 32. Consequently, it is possible to achieve the bone fusion between the vertebral bodies 101, 102 and the porous part 21 promptly.

In the present invention, a titanium based material such as titanium or a titanium alloy is mainly used as a constituent material of such a block body 2, namely constituent materials of the dense part 25 and the porous part 21.

The titanium based material has high biocompatibility and excellent strength, and therefore is used as the constituent material of the block body 2 reliably. In the titanium based material, the titanium alloy is preferably used as the constituent material of the dense part 25 requiring the excellent strength in a constituent member of the block body 2. This is because the titanium alloy has more excellent strength. Further, examples of the titanium alloy are not limited particularly, but include an alloy in which one or more of Al, Sn, Cr, Zr, Mo, Ni, Pd, Ta, Nb, V, Pt and the like are added to Ti of a main component, and the like. Examples of such an alloy include Ti-6Al-4V, Ti-29Nb-13Ta-4.6Zr and the like.

The pair of block bodies 2 as described above is inserted between the vertebral body 101 and the vertebral body 102 (intervertebral space) side by side with each other.

By inserting the block body 2 into the intervertebral space, a space 103 is formed in an area of the intervertebral space in which no block body 2 exists. A grafted bone (particular, autologous bone) as a filler is filled into the space 103, so that it is ensured to achieve the bone fusion between the vertebral body 101 and the vertebral body 102 through the block body 2 and the grafted bone more reliably and promptly.

Further, the spacer 1 is constituted from the pair of block bodies 2, 2. Therefore, if the arrangement of the block bodies 2, 2 is changed, that is, they are arranged in a state of spacing the front ends or the back ends of the block bodies 2 from each other and/or approaching them to each other, it becomes possible to treat an appropriate cure depending upon cases.

The spacer 1 as described above, for example, can be produced as follows.

<1> First, prepared is a frame-shaped dense body to become the dense part 25 by performing a debinding process and sintering process.

Such a frame-shaped dense body can be obtained easily by preparing a sheet-shaped dense body constituted of the titanium based material and cutting the sheet-shaped dense body in a predetermined shape and size by using a slice cut method such as a laser cut method, a water jet method, a discharge wire method and an ultrasound ablation method. Alternatively, the frame-shaped dense body is prepared by using a slurry of which concentration is adjusted so that the porosity thereof is more smaller, which is the same process as that of a green body to become the porous part 21 as described later. Moreover, the frame-shaped dense body is also prepared by using a slurry of which composition and an additive amount of a foaming agent (0% to) are adjusted, which is the same process as that of the green body to become the porous part 21 as described later.

<2> Next, prepared is a green body to become the porous part 21 by performing a debinding process and a sintering process.

<2-1> First, prepared is a slurry containing metal powder and a foam agent. Powder constituted of the titanium based material described above or an oxidant thereof is used as the metal powder.

Further, an average particle size of particles of the metal powder is not limited particularly, but preferably in the range of about 0.5 to 50 μm and more preferably in the range of about 3 to 30 μm. By using the metal powder including the particles having such a size, it becomes possible to set the porosity of the obtained porous part 21 and an average pore size of pores thereof to a predetermined value. In this regard, it is to be noted that the average particle size of the particles of the metal powder can be obtained by a laser diffractometry and the like.

An amount of the metal powder in the slurry is preferably in the range of about 30 to 80 mass % and more preferably in the range of about 40 to 70 mass %. By setting the amount of the metal powder to such ranges, it becomes possible to reliably set the porosity of the obtained porous part 21 and the average pore size of the pores thereof to the predetermined value.

Examples of the foam agent is not limited particularly, but include a surfactant, a volatile organic solvent and the like. A water-insoluble hydrocarbon-based organic solvent having a carbon number of 5 to 8 is preferably used as the volatile organic solvent. Further, neopentane, hexane, heptanes and cyclohexane are more preferably used. The use of such a foam agent makes it possible to obtain the porous part 21 having a high porosity with ease.

Such a slurry contains a water-soluble resin binder and water. In addition to that, the slurry contains other components such as a plasticizer, an organic solvent and the like, if needed.

Examples of the water-soluble resin binder include methylcellulose, hydroxyl propyl methylcellulose, polyvinyl butyral, polyvinyl alcohol and the like. These materials may be used singly or in combination of two or more of them. A skeleton of the porous part 21 is formed well by using the slurry containing the water-soluble resin binder.

Examples of the plasticizer include glycerin, ethylene glycol, polyethylene glycol, and the like.

Examples of the organic solvent include methanol, ethanol, isopropanol, and the like.

<2-2> Next, the prepared slurry is applied onto a base in a sheet shape, then the applied slurry is heated and foamed and thereafter is dried to obtain a green body (green sheet).

A method of molding the slurry in the sheet shape is not limited particularly, but is preferably a doctor blade method.

The heating process is not limited particularly, but is preferably performed under a high humidity atmosphere having humidity of 80% or more. By controlling a temperature condition at this time, it is possible to uniformly control pore sizes of a huge number of foam pores formed by acts of the foam agent in the whole of the slurry. As a result, it is possible to form a three dimensional skeleton constituted of the slurry containing the metal powder.

At this time, the foam pores are formed in a flat shape on a contact surface (back surface) between the slurry and the base. On the other hand, on a surface (front surface) of the slurry opposite to the base, foam pores inflated three-dimensionally due to free foam are formed. Therefore, according to the producing method as the present embodiment, a green body having an asymmetric foam structure on the back surface and the front surface each other is formed.

Further, the drying process of the slurry in which the foam pores have been formed is performed by heating at a temperature of 100° C. or less under the atmosphere or an inert gas atmosphere. This makes it possible to reliably remove moisture contained in the slurry while maintaining the foam pores included in the slurry.

<2-3> Next, the obtained green body is peeled off from the base. Thereafter, the green body is cut in a predetermined shape and size by using the slice cut method described above. The cut green body to become the porous part 21 by performing the debinding process and sintering process is obtained.

<3> Next, the cut green body (porous part 21 before performing the debinding process and sintering process) is placed into the flame-shaped dense body (dense part 25 before performing the debinding process and sintering process), and thereafter they are heated in this state. By performing the debinding process and sintering process of the cut green body and the flame-shaped dense body, a block body 2 is obtained as the porous part 21 and the dense part 25. In this regard, it is to be noted that the porosity of the dense part 25 after performing the debinding process and sintering process is preferably in the range of 3 to 50%.

The cut green body and the flame-shaped dense body are debinded at a temperature within the range of about 350 to 600° C. for about 1 to 10 hours. The debinding under such conditions makes it possible to decompose and remove components other than the metal powder included in the cut green body and the flame-shaped dense body while maintaining a foam pore structure. Consequently, it is possible to change the cut green body and the flame-shaped dense body to a metal brown body having a skeleton structure in which the metal powder is aggregated.

Further, the cut green body and the flame-shaped dense body (metal brown body) after performing the debinding process are sintered at a temperature within the range of about 1100 to 1350° C. for about 1 to 10 hours under a non-oxidizing atmosphere. The sintering process under such conditions makes it possible to sinter the metal powder while maintaining the foam pore structure. In addition to that, it is possible to diffuse the metal powder in the cut green body and the flame-shaped dense body after performing the debinding process. As a result, the dense part 25 and the porous part 21 are diffusion-bonded together. Further, it is possible to sinter the metal powder while maintaining the foam pore structure, so that it is possible to obtain the block body 2 in which the dense part 25 and the porous part 21 are bonded together firmly.

In this regard, a degree of vacuum in the non-oxidizing atmosphere is preferably $5.0 \times 10^{-2}$ Pa or less. The non-oxidizing atmosphere is preferably an argon atmosphere.

As described above, by performing the debindng process and the sintering process, the cut green body and the flame-shaped dense body change to the porous part 21 and the dense part 25, respectively, thereby enabling a block body 2 in which the porous part 21 and the dense part 25 are bonded (integrated) together firmly to obtain.

In the case where the flame-shaped dense body is constituted of the titanium based alloy (material), frame-shaped dense bodies are formed separately in advance, and then the separately formed frame-shaped dense bodies and the porous part 21 (sintered cut green body) are assembled. Next, end portions of the separately formed frame-shaped dense bodies are welded to each other by laser and the like to obtain an assembled body. Thereafter, the assembled body is subjected to a heating treatment at a temperature in the range of 800 to 1050° C. for 1 to 10 hours under the non-oxidizing atmosphere (argon atmosphere or vacuum). This makes it possible to change the frame-shaped dense bodies to the dense part 25 and obtain a block body 2 by diffusion-bonding between the dense part 25 and the porous part 21. In this regard, when the separately formed frame-shaped dense bodies and the porous part 21 are assembled, the porous part 21 included in the assembled body formed so that each surface becomes a flat surface is used. That is, the porous part 21 in which grooves capable of containing the frame-shaped dense bodies are formed is used.

Second Embodiment

Next, description will be made on a second embodiment of a vertebral body space according to the present invention.

Figure 4:
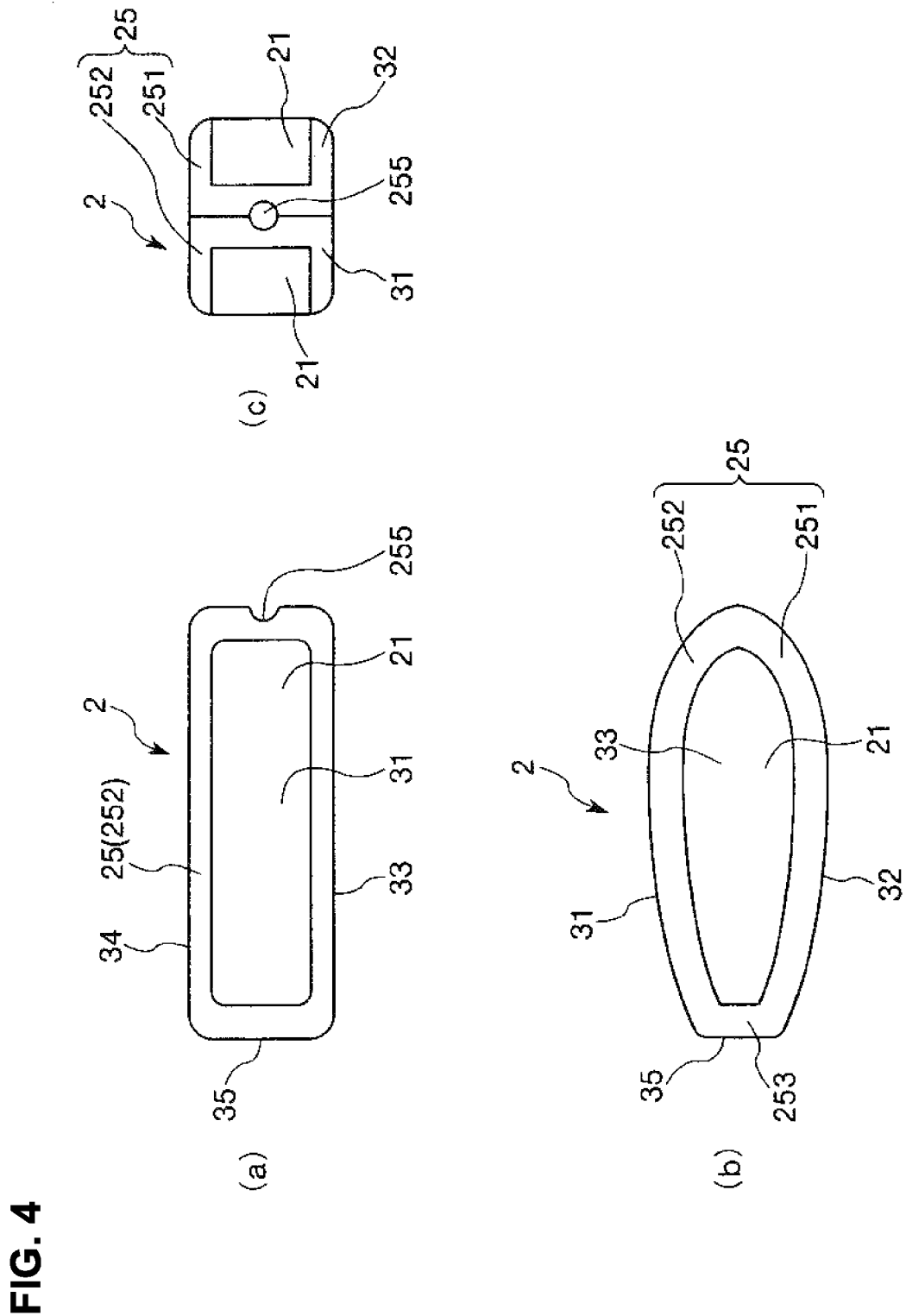
FIG. 4 is a plan view (a), a front view (b) and a side view (c) which show a second embodiment of a block body constituting a vertebral body spacer of the present invention.

FIG. 4 is a plan view (a), a front view (b) and a side view (c) which show the second embodiment of a block body constituting the vertebral body spacer of the present invention.

In the following description, the description will be made on a block body 2 shown in FIG. 4. The description will be made by focusing on different points from the block body 2 shown in FIG. 1 to FIG. 3 and the description on the common points is omitted.

The block body 2 shown in FIG. 4 is the same as the block body 2 shown in FIG. 1 to FIG. 3 except that a shape of the whole thereof is different.

In the present embodiment, both a first surface and a second surface 32 constitute a curved convex surface. The first surface 31 and the second surface 32 are connected to each other at an end portion on a front side. Thus, a sixth surface 36 is omitted. Further, each of a third surface 33, a fourth surface 34 and a fifth surface 35 constitutes substantially a flat surface. As described above, since both the first surface 31 and the second surface 32 of the block body 2 constitute the curved convex surface, it is possible to insert the block body 2 into the intervertebral space so as to slide that along the curved convex surface. For this reason, it is possible to perform an inserting operation into the intervertebral space more easily whit making the block body 2 no contact with the vertebral bodies 101 and 102.

Further, in the present embodiment, a hole portion 255 is provided at a substantial center of a dense part which forms a bonding part between the first surface 31 and the second surface 32. In the case where the block body 2 is inserted into the intervertebral space by using a jig, this hole portion 255 is used to fix the block body 2 to the jig by inserting a convex portion of the jig thereinto. This makes it possible to insert the block body 2 into the intervertebral space with ease by using the jig.

The block body 2 having such a whole shape has a lower frame portion 251 and an upper frame portion 252 which have a shape corresponding to the shape of the block body 2 in the plane view as shown in FIG. 4(a). The block body 2 also has a connecting portion 253 which connects the lower frame portion 251 and the upper frame portion 252. In the present embodiment, the connecting portion 253 is constituted from one wide connecting portion provided at an end portion on a back side of the frame portion 251 and the frame portion 252. Further, each of the frame portion 251 and the frame portion 252 is curved and directly connected at the end portion on the front side to each other. Thus, a connecting portion is omitted at the end portion on the front side of the frame portion 251 and the frame portion 252.

The block body 2 of the present embodiment configured as described above can be also used as the block body 2 of the first embodiment and obtain the same effects as those of the block body 2 (spacer 1) of the first embodiment.

Third Embodiment

Next, description will be made on a third embodiment of a vertebral body space according to the present invention.

Figure 5:
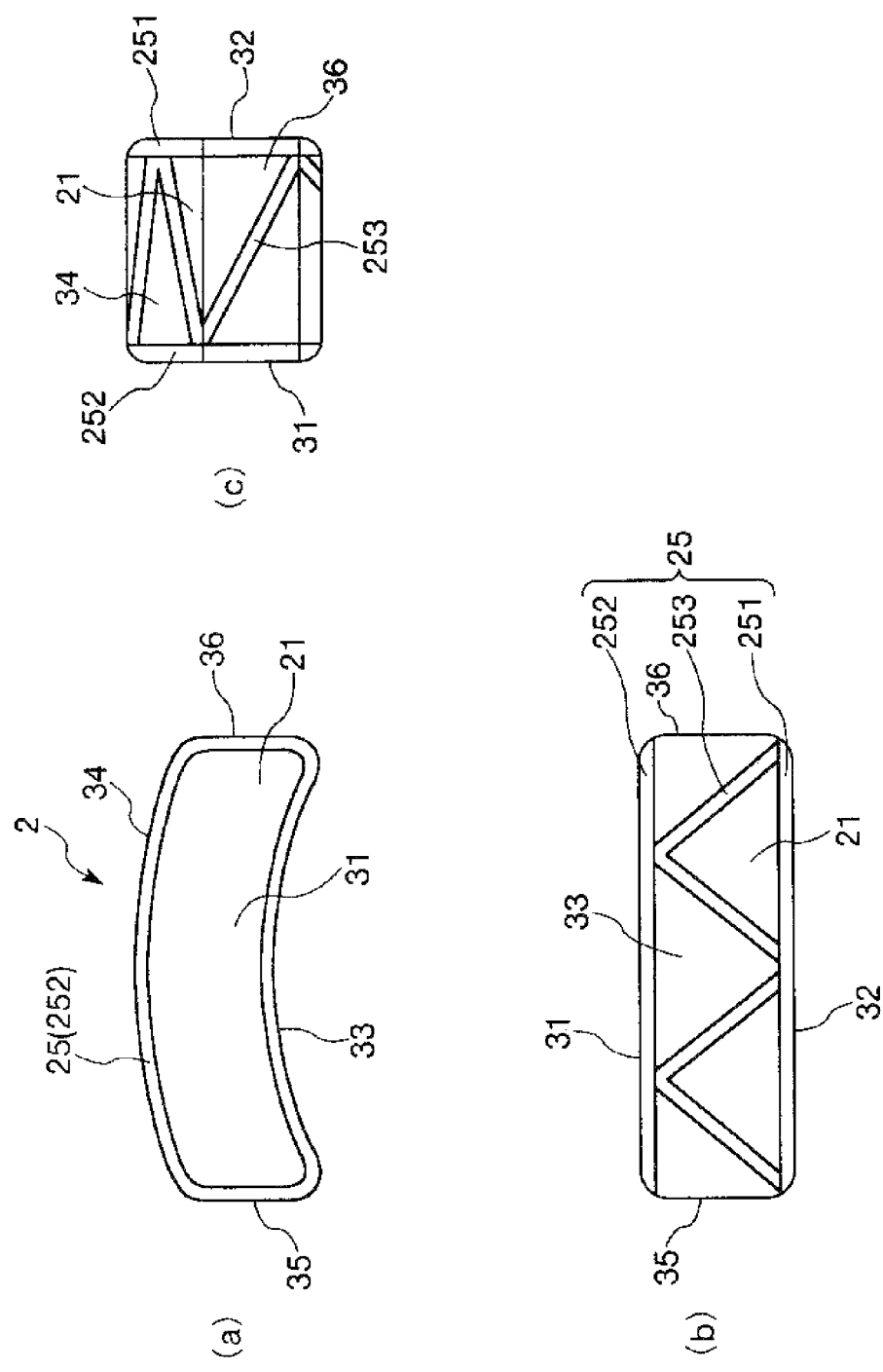
FIG. 5 is a plan view (a), a front view (b) and a side view (c) which show a third embodiment of a block body constituting a vertebral body spacer of the present invention.

FIG. 5 is a plan view (a), a front view (b) and a side view (c) which show the third embodiment of a block body constituting the vertebral body spacer of the present invention.

In the following description, the description will be made on a block body 2 shown in FIG. 5. The description will be made by focusing on different points from the block body 2 shown in FIG. 1 to FIG. 3 and the description on the common points is omitted.

The block body 2 shown in FIG. 5 is the same as the block body 2 shown in FIG. 1 to FIG. 3 except that a configuration of the dense part 25 is different.

In the present embodiment, as shown FIG. 5, each of connecting portions 253 is placed diagonally in an upper-lower direction of the block body 2. The adjacent connecting portions 253 make contact with (connect to) each other at an end portion thereof (a portion connecting a lower frame portion 251 and an upper frame portion 252). In other words, a dense part 25 constituted from the lower frame portion 251, the upper frame portion 252 and the connecting portions 253 makes a truss structure. This ensures that the connecting portions 253 exhibit a function reliably of supporting the lower frame portion 251 and the upper frame portion 252 as a supporting post, thereby improving strength of the dense part 25. Therefore, it is possible to reliably suppress or prevent the dense part 25 from being broken when stress is applied to the block body 2 in the inserted state.

The block body 2 of the present embodiment configured as described above can be also used as the block body 2 of the first embodiment and obtain the same effects as those of the block body 2 (spacer 1) of the first embodiment.

Fourth Embodiment

Next, description will be made on a fourth embodiment of a vertebral body space according to the present invention.

Figure 6:
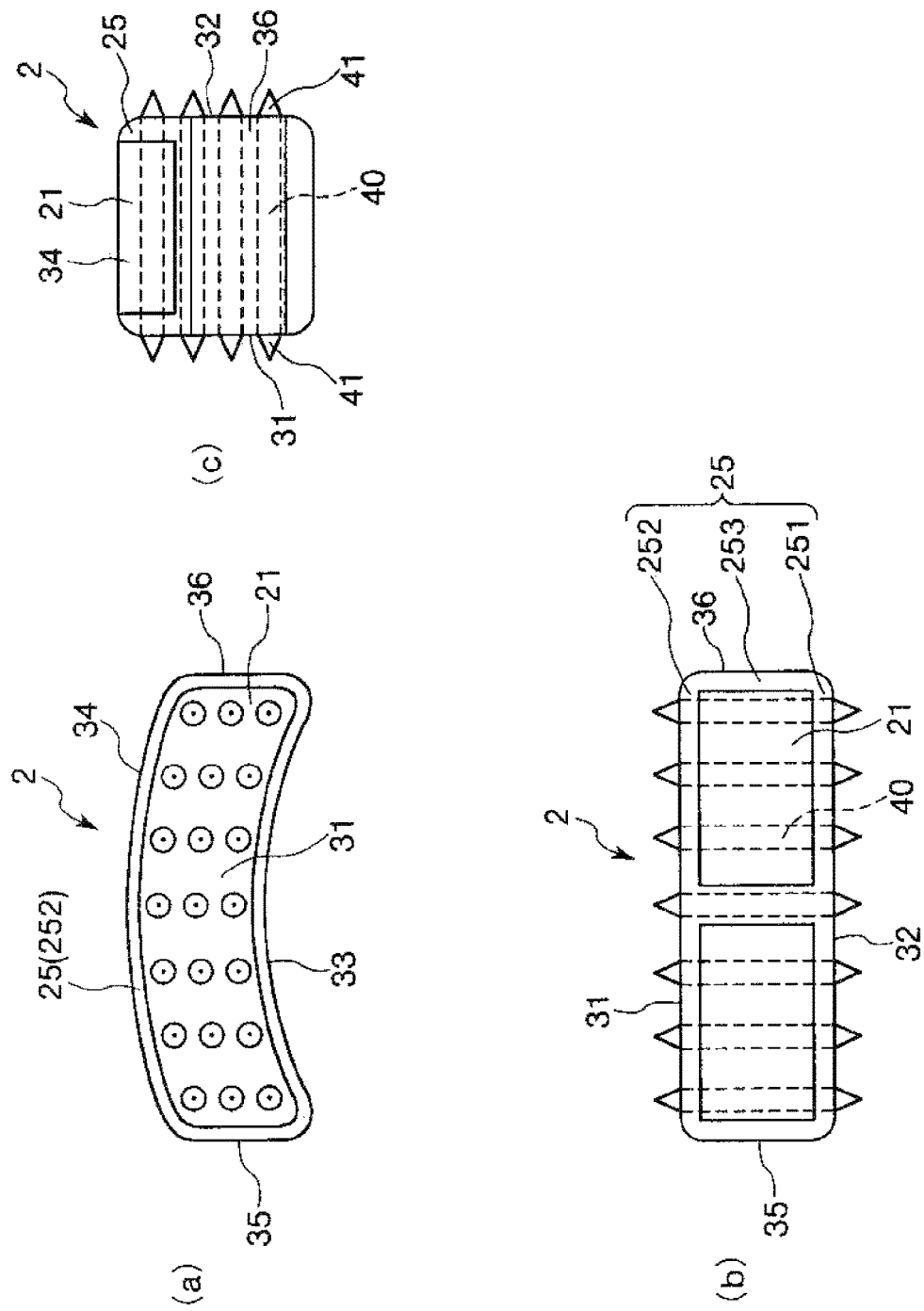
FIG. 6 is a plan view (a), a front view (b) and a side view (c) which show a fourth embodiment of a block body constituting a vertebral body spacer of the present invention.

FIG. 6 is a plan view (a), a front view (b) and a side view (c) which show the fourth embodiment of a block body constituting the vertebral body spacer of the present invention.

In the following description, the description will be made on a block body 2 shown in FIG. 6. The description will be made by focusing on different points from the block body 2 shown in FIG. 1 to FIG. 3 and the description on the common points is, omitted.

The block body 2 shown in FIG. 6 is the same as the block body 2 shown in FIG. 1 to FIG. 3 except that a plurality of conical projection portions 41 is provided so as to project from a first surface 31 and a second surface 32.

In the present embodiment, needle bodies 40 having projection portions 41 at both ends thereof are inserted into a plurality of through holes provided to pass through a porous part 21 so that the projection parts 41 are projected from the porous part 21. As described above, the plurality of projection portions 41 projecting from the first surface 31 and the second surface 32 is provided with the block body 2. Therefore, the projection portions 41 is spiked (anchored) on the lower surface of the vertebral body 101 and the upper surface of the vertebral body 102 when the block body 2 is inserted into the intervertebral space. By doing so, it is possible to make the first surface 31 and the second surface 32 firm contact with the vertebral body 101 and the vertebral body 102, respectively. Consequently, it is possible to reliably prevent the block body 2 from dropping off from the intervertebral space.

It is preferred that the needle bodies 40 configured as described above are constituted from a dense part like the dense part 25. The needle bodies 40 exhibit more excellent strength, so that it is possible to reliably prevent or suppress the needle bodies 40 from being broken when stress is applied to the block body 2 in the inserted state.

The block body 2 of the present embodiment configured as described above can be also used as the block body 2 of the first embodiment and obtain the same effects as those of the block body 2 (spacer 1) of the first embodiment.

In this case, it is to be noted that a shape of each of the projection portions 41 is not limited to the conical shape as shown in FIG. 6, for example, it may be a pyramid shape such as a quadrangular pyramid shape or a triangular pyramid shape.

Fifth Embodiment

Next, description will be made on a fifth embodiment of a vertebral body space according to the present invention.

Figure 7:
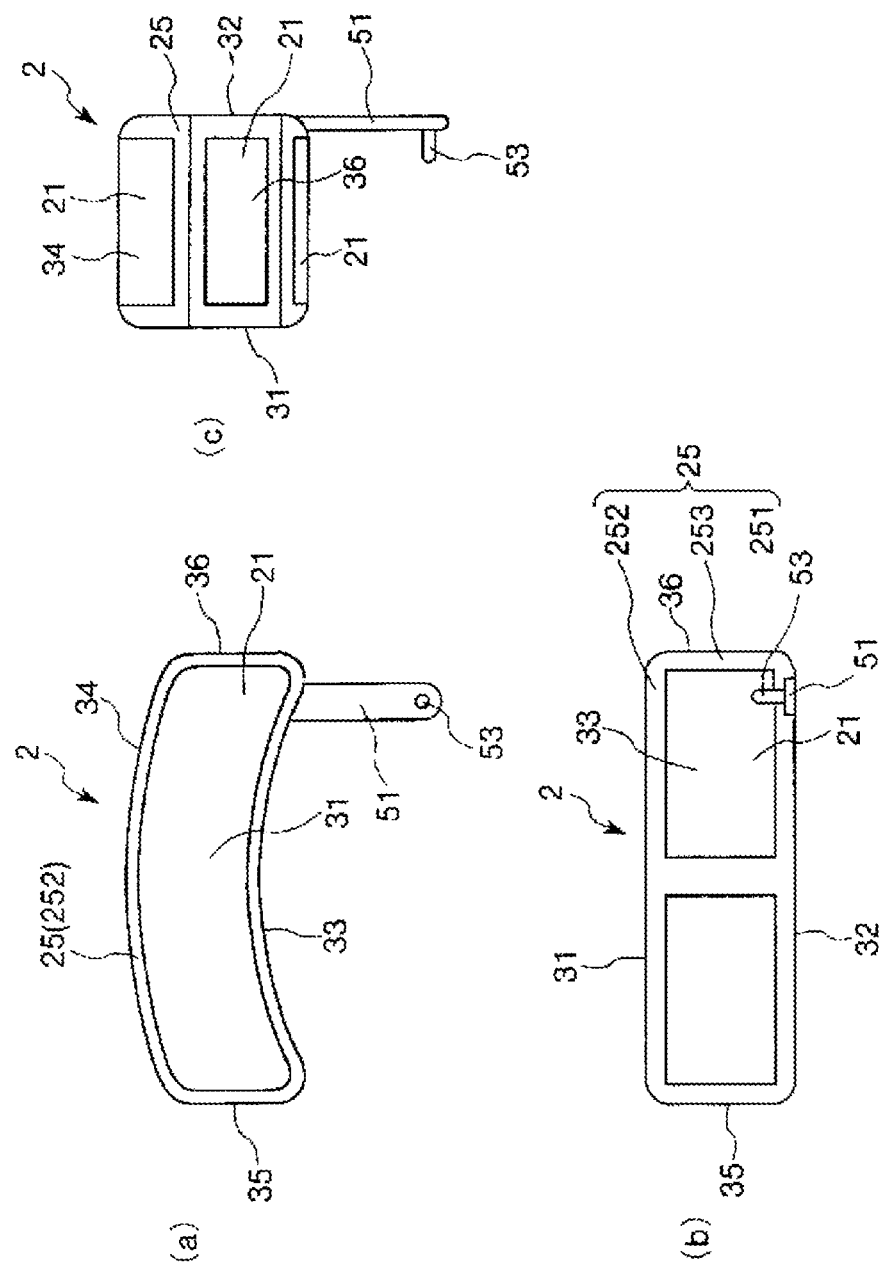
FIG. 7 is a plan view (a), a front view (b) and a side view (c) which show a fifth embodiment of a block body constituting a vertebral body spacer of the present invention.

FIG. 7 is a plan view (a), a front view (b) and a side view (c) which show a fifth embodiment of a block body constituting a vertebral body spacer of the present invention.

Figure 8:
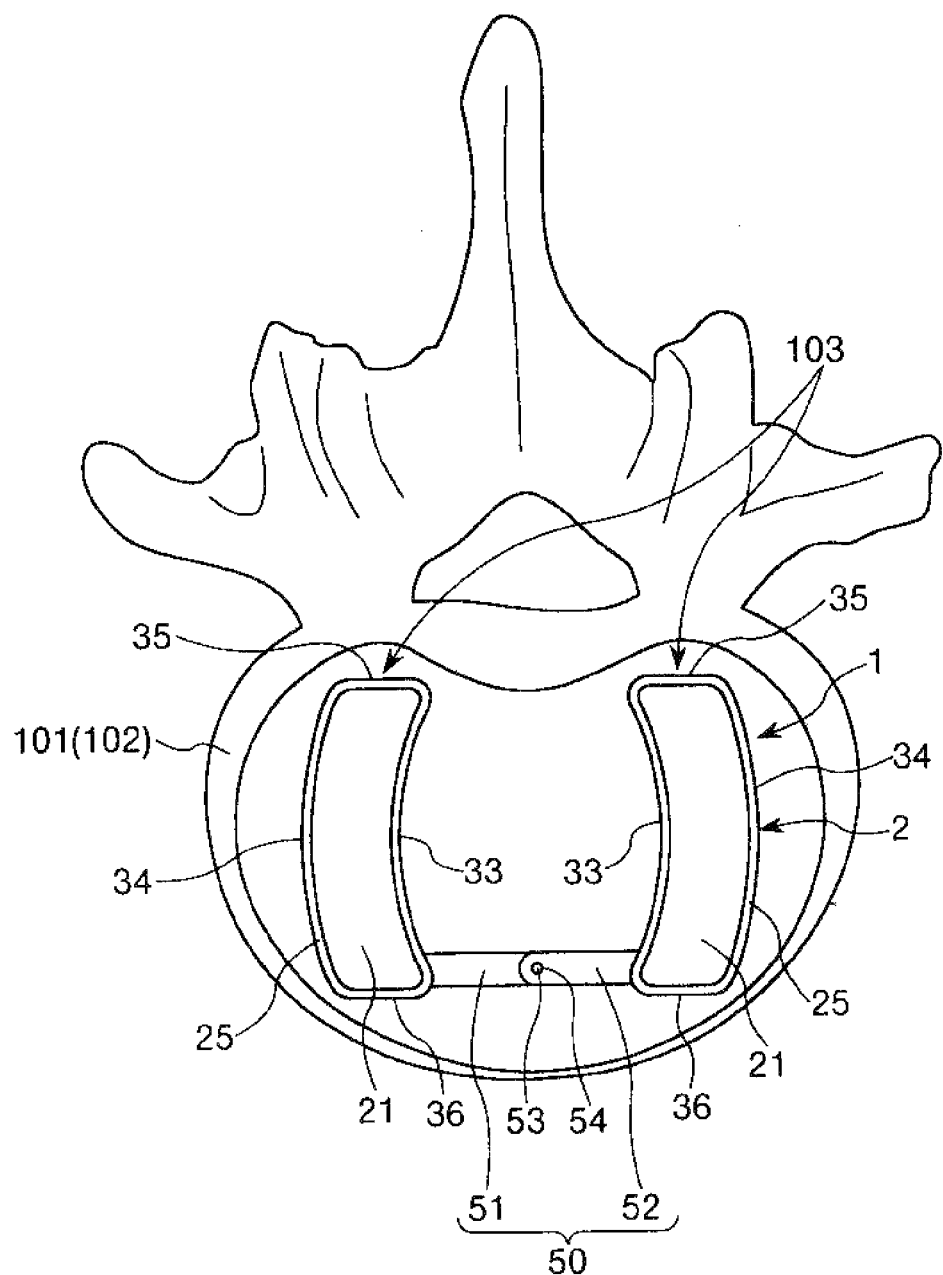
FIG. 8 is a view showing a used state of the fifth embodiment of the vertebral body spacer of the present invention.

In the following description, the description will be made on a block body 2 shown in FIGS. 7 and 8. The description will be made by focusing on different points from the block body 2 shown in FIG. 1 to FIG. 3 and the description on the common points is omitted.

The block body 2 shown in FIG. 7 is the same as the block body 2 shown in FIG. 1 to FIG. 3 except that a connecting portion 50 of rotatably connecting a pair of block bodies 2 to each other is provided with the pair of block bodies 2.

In the present embodiment, the connecting portion 50 has a plate-shaped connection finger 51 provided at an end portion on a front side of a third surface 33 of one of the block bodies 2 and a plate-shaped connection finger 52 provided at an end portion on a front side of a third surface 33 of the other of the block bodies 2. A road-shaped body 53 is formed at an end portion on a side of the connection finger 51 opposite to the block body 2 so as to project toward an upper direction. A through hole 54 is formed at an end portion on a side of the connection finger 52 opposite to the block body 2. The two block bodies 2 are connected to each other through the connecting portion 50 by inserting the rod-shaped body 53 into the through hole 54. Further, a hinge portion is formed by inserting the rod-shaped body 53 into the through hole 54, so that it is possible for the block bodies to approach to and space from each other at the hinge portion as a center of rotation. In other words, the block bodies 2 are capable of rotating in a horizontal direction with respect to a first surface 31.

According to the spacer 1 having such an configuration, it is possible to change a position of each block body 2, namely to perform operations easily and rapidly of spacing front ends and back ends of block bodies 2 from each other and/or approaching them to each other, which depend on cases. Therefore, it becomes possible to perform an appropriate cure by using such a spacer 1 promptly. Further, since the block bodies 2 are connected to each other through the connecting portion 50, it is easy to accurately position them in the intervertebral space in the inserted state.

The block body 2 of the present embodiment configured as described above can be also used as the block body 2 of the first embodiment and obtain the same effects as those of the block body 2 (spacer 1) of the first embodiment.

The description has been made on the embodiments of the vertebral body space according to the present invention as shown in the drawings. However, the present invention is not limited to them.

For example, any configuration of the first to fifth embodiments may be combined arbitrarily in the vertebral body space according to the present invention.

Further, in each of the embodiments, the porous part 21 is constituted from one member, however, may be constituted by laminating (attaching) a plurality of sheet-shaped bodies each having a different porosity. In this case, it is possible to give anisotropy to the strength of the porous part 21, thereby improving flexibility in a design of the block body 2 (spacer 1).

Further, in each of the embodiments, the description has been made on the case of inserting the pair of block bodies 2 into the intervertebral space. However, the case is not limited thereto, and may be a case of inserting one block body 2 into the intervertebral space. In this case, the block body 2 is inserted in the front side of the intervertebral space so that the fourth surface 34 faces to the front side and the third surface 33 faces to the back side.

Moreover, the filler is not limited to the grafted bone (autologous bone), for example, may be powder or granule of a calcium phosphate based compound, a calcium phosphate based cement and the like.

INDUSTRIAL APPLICABILITY

The vertebral body spacer of the present invention is capable of maintaining an appropriate size between vertebral bodies (intervertebral space). Further, the vertebral body spacer of the present invention is capable of reliably preventing the vertebral body spacer from being broken irrespective of cases and a position of the intervertebral space, and thereby capable of achieving bone fusion between the vertebral body spacer and the vertebral bodies promptly. Moreover, a space of filling the filler into the intervertebral space is ensured by inserting the vertebral body spacer thereinto. For these reasons, by filling the grafted bone to such a space, it is possible to reliably and promptly achieve the bone fusion between the vertebral bodies through the vertebral body spacer and the grafted bone. Accordingly, the present invention has industrial applicability.

What is claimed is:

1. A vertebral body spacer to be used by being inserted between vertebral bodies, comprising;
   a pair of block bodies, each block body having a pair of contact surfaces configured to contact the vertebral bodies, and
   a connecting portion rotatably connecting the pair of block bodies to each other,
   wherein the block body includes a frame-shaped dense part having a porosity of 10 to 40% and a porous part provided inside the dense part, and a porosity of at least a surface of the porous part is larger than a porosity of the dense part, wherein the porous part and the dense part of each block body are constituted of titanium or a titanium alloy as a main component thereof,
   wherein the dense part includes a first frame portion configured to contact one of the vertebral bodies and a second frame portion configured to contact the other of the vertebral bodies,
   wherein one surface of the pair of contact surfaces is constituted from the first frame portion of the dense part and the porous part, and the other surface of the pair of contact surfaces is constituted from the second frame portion of the dense part and the porous part, and
   wherein each surface of the pair of contact surfaces constitutes a flat surface.

2. The vertebral body spacer as claimed in claim 1, wherein the dense part and the porous part are integrally formed.

3. The vertebral body spacer as claimed in claim 1, wherein the porous part has a plurality of corner portions, and the dense part is provided along the plurality of corner portions of the porous part.

4. The vertebral body spacer as claimed in claim 1, wherein the block body is constituted from a polyhedral body defined by a plurality of surfaces including the pair of contact surfaces, and each of the plurality of surfaces constitutes a flat surface.

5. The vertebral body spacer as claimed in claim 1, wherein a whole of the porous part is constituted from a porous body.

6. The vertebral body spacer as claimed in claim 1, wherein an osteoinductive factor is carried on the porous part.

7. The vertebral body spacer as claimed in claim 1, wherein the dense part includes at least one connecting portion connecting the first frame portion and the second frame portion to each other, and wherein the connecting portion serves as a supporting post.

8. The vertebral body spacer as claimed in claim 1, wherein the block body is constituted from a polyhedral body defined by a plurality of surfaces having the pair of contact surfaces, a first surface connecting the pair of contact surfaces at a front end of the block body and a second surface connecting the pair of contact surfaces at a back end of the block body, and
   wherein the first surface and the second surface constitute a flat surface.

* * * * *